(12) United States Patent
Karkanias et al.

(10) Patent No.: US 7,993,291 B2
(45) Date of Patent: Aug. 9, 2011

(54) HAPTIC SUPPORT AND VIRTUAL ACTIVITY MONITOR

(75) Inventors: Chris Demetrios Karkanias, Sammamish, WA (US); Stephen Edward Hodges, Cambridge (GB)

(73) Assignee: Microsoft Corporation, Redmond, WA (US)

( * ) Notice: Subject to any disclaimer, the term of this patent is extended or adjusted under 35 U.S.C. 154(b) by 428 days.

(21) Appl. No.: 11/754,486

(22) Filed: May 29, 2007

(65) Prior Publication Data

US 2008/0300521 A1    Dec. 4, 2008

(51) Int. Cl.
    *A61F 5/00* (2006.01)
(52) U.S. Cl. ............... 602/5; 602/16; 602/20; 602/23; 602/26
(58) Field of Classification Search ............ 602/5, 16, 602/21–23, 26–27; 128/882; 600/587–595
See application file for complete search history.

(56) References Cited

U.S. PATENT DOCUMENTS

| | | | |
|---|---|---|---|
| 5,429,140 A | | 7/1995 | Burdea et al. |
| 5,709,219 A | | 1/1998 | Chen et al. |
| 5,774,376 A | | 6/1998 | Manning |
| 5,929,782 A | * | 7/1999 | Stark et al. ............... 340/870.01 |
| 5,954,621 A | * | 9/1999 | Joutras et al. ............... 482/114 |
| 5,980,435 A | * | 11/1999 | Joutras et al. ............... 482/114 |
| 5,984,880 A | | 11/1999 | Lander et al. |
| 6,149,586 A | | 11/2000 | Elkind |
| 6,436,058 B1 | * | 8/2002 | Krahner et al. ............... 600/587 |
| 6,454,681 B1 | | 9/2002 | Brassil et al. |
| 6,478,735 B1 | | 11/2002 | Pope et al. |
| 6,726,638 B2 | | 4/2004 | Ombrellaro |
| 6,817,973 B2 | | 11/2004 | Merril et al. |
| 7,023,423 B2 | | 4/2006 | Rosenberg |
| 7,128,577 B2 | | 10/2006 | Renaud |
| 7,206,626 B2 | | 4/2007 | Quaid, III |
| 7,206,627 B2 | | 4/2007 | Abobitz et al. |
| 2004/0254771 A1 | | 12/2004 | Riener et al. |
| 2008/0277943 A1 | * | 11/2008 | Donelan et al. ............... 290/1 R |

FOREIGN PATENT DOCUMENTS

WO    WO 2004000131 A1    12/2003

OTHER PUBLICATIONS

International Search Report and Written Opinion for PCT Application No. PCT/US2008/064819, mailed Oct. 30, 2008, 10 pages.

(Continued)

*Primary Examiner* — Michael A. Brown
(74) *Attorney, Agent, or Firm* — Turocy & Watson, LLP

(57) ABSTRACT

A system that can monitor motion and establish haptic feedback to promote rehabilitation and/or strength training is provided. The innovation can be applied at any point along a rehabilitative progression continuum to provide computer-regulated (e.g., virtual, remote) training and/or coaching. For example, the innovation can be employed to actively drive a limb, provide force feedback to promote wellness, passively monitor motion of a limb or even to establish resistance to encourage strength training. The modular components of the system promote adaptability to users of all shapes and sizes.

11 Claims, 10 Drawing Sheets

OTHER PUBLICATIONS

Soichiro Matsushita, et al. A wearable Sense of Balance Monitoring System towards Daily Health Care Monitoring. http://www.cse.eng.toyo.ac.jp/gmatsu/nanoint/YuraYuraISWC04.pdf. Last accessed Nov. 13, 2006.

Grigore Burdea, et al. Virtual Reality Training for the Diagnosis of Prostate Cancer. http://citeseer.ist.psu.edu/cache/papers/cs/2917/http:zSzzSzwww.caip.rutgers.eduzSzvrlabzSzPAPERSzSzvrais98.pdf/burdea98virtual.pdf. Last accessed Nov. 13, 2006.

Ming-Chang Lee, et al. Mems Bio-Vibration Sensor. http://www.ee.ucla.edu/~wu/ee250b/Projects_2001/Group_6_Report_Bio%20Vibration.pdf. Last accessed Nov. 13, 2006.

Mario Gutierrez, et al. Telerehabilitation: Controlling Haptic Virtual Environments through Handheld Interfaces. http://delivery.acm.org/10.1145/1080000/1077577/p195-gutierrez.pdf?key1=1077577&key2=1118313611&coll=GUIDE&dl=GUIDE&CFID=4217365&CFTOKEN=59543854. pp. 195-200. Last accessed Nov. 13, 2006.

* cited by examiner

US 7,993,291 B2

HAPTIC SUPPORT AND VIRTUAL ACTIVITY MONITOR

BACKGROUND

Physical therapy refers to a service industry where healthcare professionals render services to patients in an effort to establish, maintain, rehabilitate or restore motion and functional ability. Oftentimes, physical therapy is used as a result of an injury (e.g., automobile accident, sports injury). In other instances, physical therapy is used in aging patients to regain or maintain motion or functional ability.

Throughout the process of physical therapy, oftentimes orthopedic devices such as braces are employed to promote healing and to prevent further damage to bones, muscles or ligaments. For example, knee braces are often used to restrict motion of a knee joint following an injury or surgery. These braces are available in a variety of types such as elastic braces, hinged braces, magnetic braces, neoprene braces, etc. As well, braces are specifically sized for comfort and performance based upon a particular patient.

A physical therapist is much like a coach in that they provide hands-on therapy, or coaching, during the process of therapy. These therapists are persons trained or certified by a state or accrediting body to design and/or implement physical therapy programs. Physical therapists work in a large range of environments that include a hospital or clinic, a school to provide assistance to special education students or even as an independent contractor, for example, to a sports team. While the services provided by these therapists is essential to the well-being of their patients, these services are very expensive, oftentimes not covered by insurance carriers. Further, oftentimes geographic limitations further inhibit the ability to provide or receive effective treatment on a regular basis.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in one aspect thereof, comprises a system that can monitor motion and establish haptic feedback to promote rehabilitation and/or strength training. In the health strategies space, the innovation can provide force feedback where, for instance, a patient has been prescribed a specific therapeutic routine. While performing the therapy, data can be gathered and later analyzed. By way of specific example, if an individual sprains a knee, a doctor might prescribe a haptic brace where therapy can be regulated from a remote location. In one aspect, the haptic brace can be connected to a personal computer, game console or some other computing device and, through the use of a joystick, the physical therapy and ranges of motion necessary to promote rehabilitation can be controlled. Effectively, the haptic brace of the innovation can enable virtual physical therapy.

In accordance with this innovation, other physiological and/or environmental sensors can be employed to gather information in accordance with virtual physical therapy. This haptic system can also be used in the course of everyday workouts. Thus, the innovation can perform as a virtual personal trainer to enhance and regulate physical activity. In other aspects, the innovation can be employed in many different areas such as a virtual coach, etc. In particular examples, this idea can be used for yoga in terms of posture, golf in terms of swing characteristics and motion, etc.

Essentially, the features, functions and benefits of the innovation can be applied at any point along a rehabilitative progression continuum. For example, the innovation can be employed to actively drive a limb, provide force feedback to promote wellness, passively monitor motion of a limb or even to establish resistance to encourage strength training. The modular components of the system promote adaptability to users of all shapes and sizes.

In yet another aspect thereof, machine learning and reasoning mechanisms are provided that employ a probabilistic and/or statistical-based analysis to prognose or infer an action that a user desires to be automatically performed.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
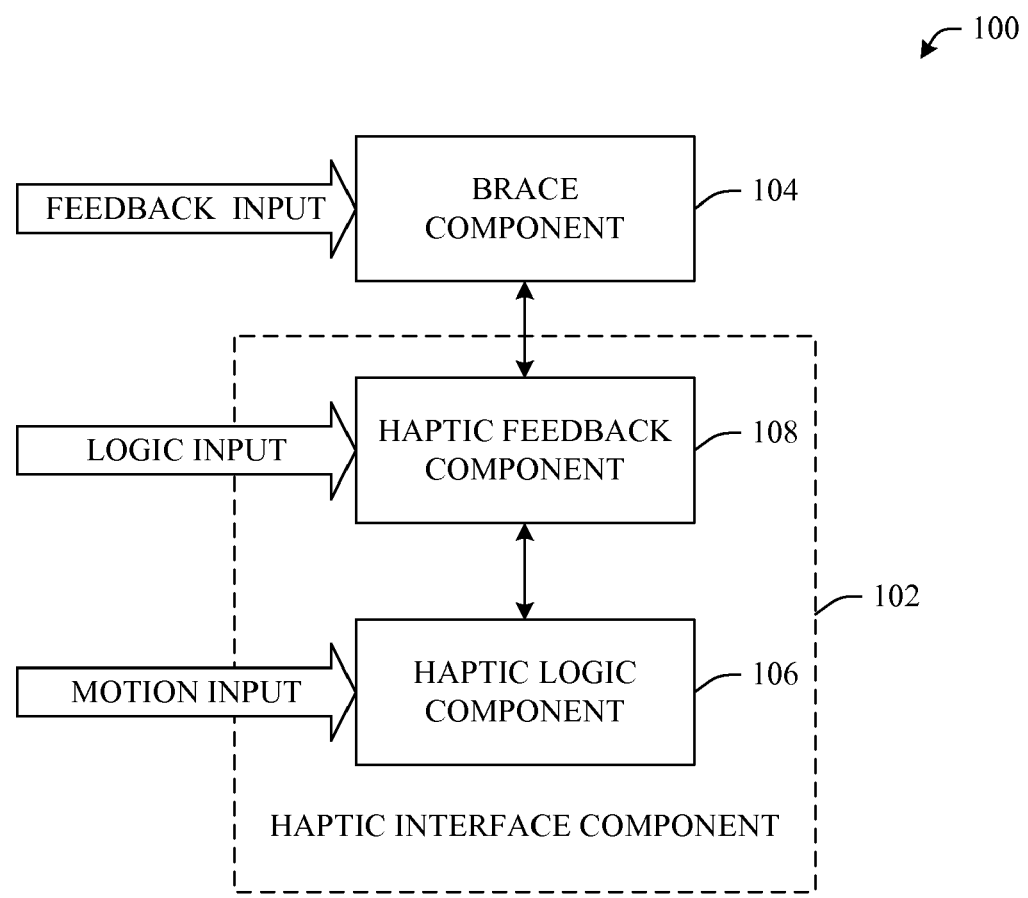
FIG. 1 illustrates a system that facilitates haptic feedback in accordance with an aspect of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term to "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

While certain ways of displaying information to users are shown and described with respect to certain figures as screenshots, those skilled in the relevant art will recognize that various other alternatives can be employed. The terms "screen," "web page," and "page" are generally used interchangeably herein. The pages or screens are stored and/or transmitted as display descriptions, as graphical user interfaces, or by other methods of depicting information on a screen (whether personal computer, PDA, mobile telephone, or other suitable device, for example) where the layout and information or content to be displayed on the page is stored in memory, database, or another storage facility.

Referring initially to the drawings, FIG. 1 illustrates a system 100 that facilitates haptics in a health-related context. It is to be understood that 'haptics' can refer to the science of applying tactile sensation to human interaction with a computer or computing devices. A haptic interface or device can refer to an apparatus that involves physical contact between the computer and the user. Conventionally, this physical contact was limited to input/output devices such as a joystick or data glove which can sense movements of one's body. Here, the innovation discloses the use of haptics in connection with health-care scenarios. Although many of the aspects described herein are specific to health-care scenarios, it is to be understood that other embodiments can employ the features, functions and benefits of the innovation to monitor joint movement for interactive gaming, feedback while exercising, virtual coaching while performing sporting activities, etc. For instance, this feedback can provide motivation, encouragement, instruction or the like. These alternative aspects are to included within the scope of this disclosure and claims appended hereto.

Generally, system 100 can include a haptic interface component 102 that can communicate tactile sensations via a brace component 104. More particularly, in one aspect, the haptic interface component 102 can function as a virtual physical therapist or coach by rendering tactile sensations and feedback to ensure compliance with some predetermined exercise routine. As will be understood upon a review of the figures that follow, this corrective feedback example is but one example of how the haptic interface component 102 can be employed in a health-related environment. Other alternative applications of the haptic interface 102 are to be included within the scope of this disclosure and claims appended hereto.

By using haptic devices, the system 100 enables users (e.g., patients) to input information to the computer as well as to receive feedback information from the computer in the form of a felt sensation on some part of the body. As will be understood, this felt sensation can be in the form of vibratory sensation, temperature fluctuation sensation, pressure sensation, among others. The ability to process the information and to deliver this feedback via a device is referred to herein as the haptic interface 102. For example, in a virtual reality environment, a user can pick up a virtual rock using a data glove. In this example, the computer can sense the movement and accordingly displace the virtual rock on the virtual display. Because of the nature of a haptic interface 102, the user can feel the rock in his hand through tactile sensations that the computer sends through the data glove, thereby mimicking the feel of the rock in the user's hand.

As shown, the haptic interface component 106 can include a haptic logic component 106 and a haptic feedback component 108. In operation, continuing with the example above, the haptic logic component 106 can monitor and analyze a patient's (or user's) motion. An output can be generated that is transmitted to a haptic feedback component 108 which, in turn, established the appropriate feedback. By way of example, the haptic feedback component 108 can establish forced feedback or resistance feedback as appropriate. This feedback can be communicated and implemented via the brace component 104.

While the system 100 can be employed in most any scenario, there are at least two general categories where the system can be employed, illness care and strength training. Although fundamentally different, each of these scenarios can greatly benefit from the overall virtual coach benefits of the innovation. In other words, the haptic interface component 102 (and subcomponents 106, 108) can provide a user or patient with sensory feedback to control, assess, monitor, correct or promote physical activity.

In operation, the functionalities of the innovation can be employed in a number of different scenarios. In a first example, the haptic interface 102 can effectively drive the brace component 104. In a second example, the haptic interface 102 can monitor and provide force feedback on an as-needed basis (e.g., in response to a deviation in a preprogrammed range of motion). In a third example, the haptic interface 102 can passively monitor motion and, if desired, can save the data for later retrieval or access. In a forth example, the haptic interface 102 can generate resistance in accordance with a desired or preprogrammed routine. Each of these four scenarios is illustrated in greater detail with reference to FIGS. 2, 3, 4 and 5 that follow.

Figure 2:
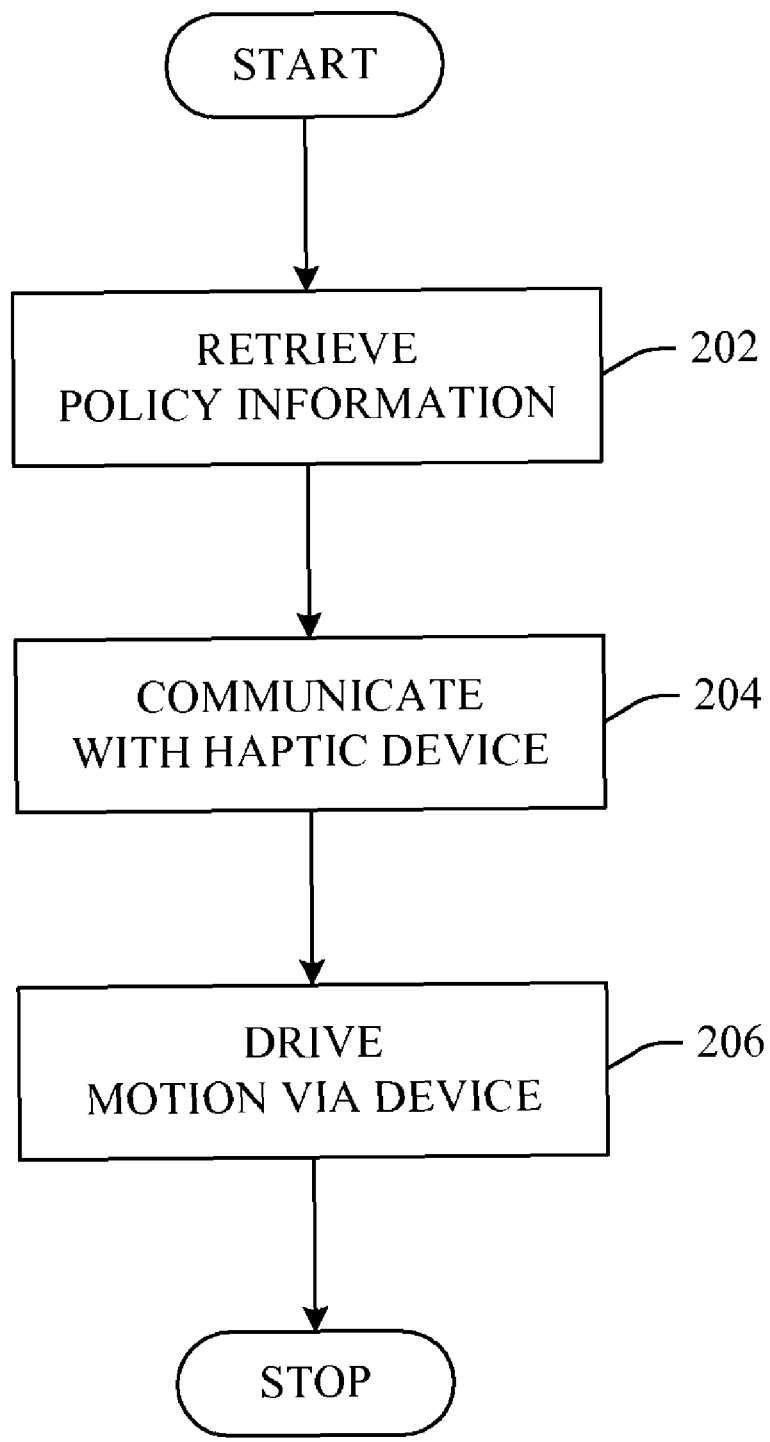
FIG. 2 illustrates an example flow chart of procedures that facilitate proactive drive of a brace in accordance with an aspect of the innovation.

FIG. 2 illustrates a methodology of proactively driving motion via a haptic device in accordance with an aspect of the innovation. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

At 202, policy information is retrieved. In aspects, it is to be understood that this information can be pushed or pulled from most any source. For example, a health-care professional or coach can provide a storage device such as a flash drive to a user. In this example, a workout routine or policy can be pre-stored on the flash drive. In other aspects, a user can download policy information from a cloud or the internet via a USB (universal serial bus), wireless (e.g., Bluetooth, 802.11, WiFi) or other suitable connection. In operation, this flash drive can be employed to provide policy information to a haptic device at 202. In yet other aspects, a user's cell phone or other mobile device can be employed to transfer policy information wirelessly (e.g., Bluetooth™) or by any other suitable means.

Once the policy information (or portion thereof) is retrieved, communication can be established with the haptic device at 204. Here, the policy information from 202 can be communicated into an interface device which effectively controls operation of the device. At 206, the device can be driven in accordance with the policy information. For example, in the case where the haptic device is a knee brace, the range of motion can be proactively driven by the brace thereby actively extending a patient's leg in accordance with a predetermined value.

Figure 3:
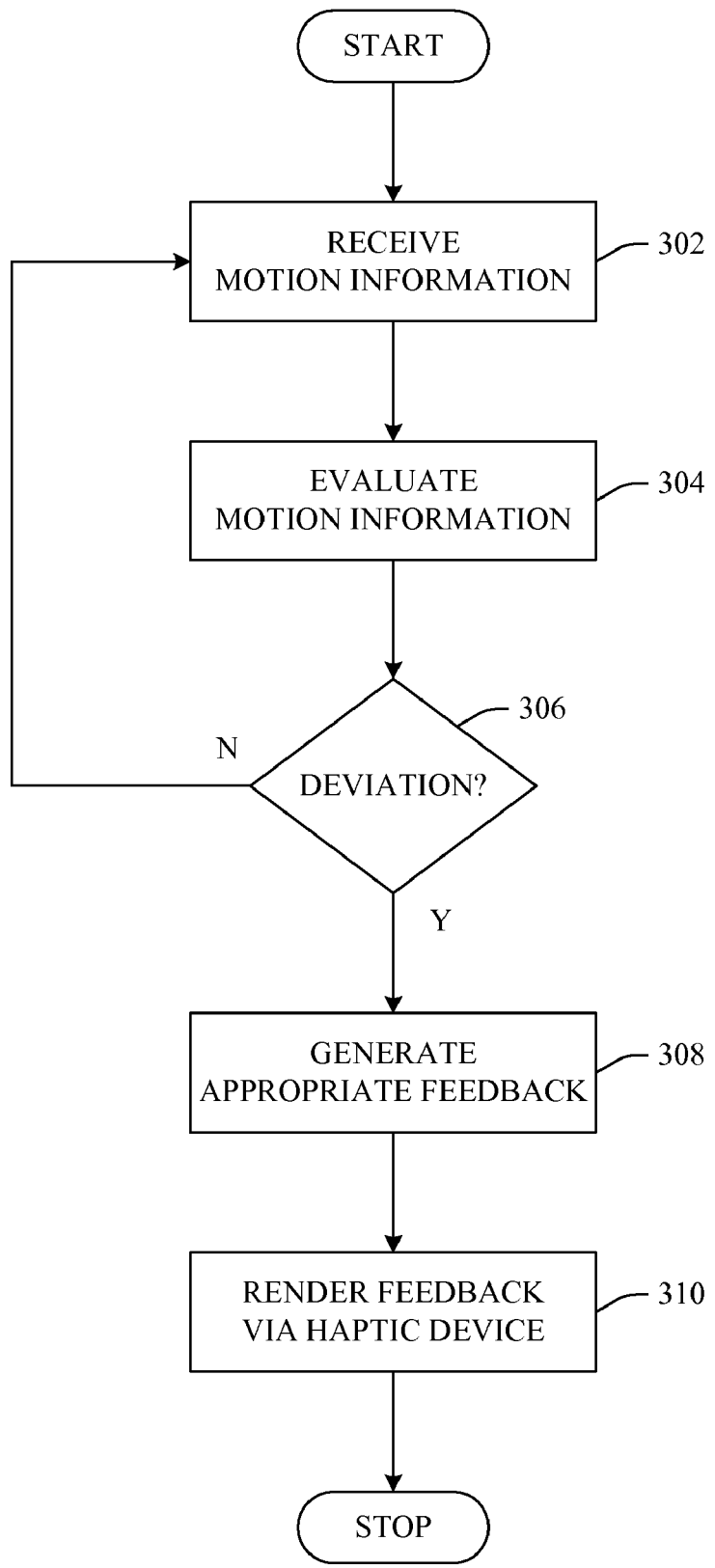
FIG. 3 illustrates an example flow chart of procedures that facilitate rendering haptic feedback in accordance with an aspect of the innovation.

With reference now to FIG. 3, there is illustrated a methodology of establishing and rendering feedback in accordance with the innovation. At 302, motion information is received that describes motion of a user. For example, continuing with the above scenario, motion of a user's leg can be actively monitored. At 304, the specifics of the motion can be evaluated in accordance with a defined or pre-determined policy set by a user or other third party (e.g., physical therapist, health-care professional). In other aspects, machine learning and reasoning (MLR) mechanisms can be employed to infer a policy or routine based upon most any number of factors including, but not limited to, date of injury, rate of progress, age of patient, time of day, history of therapy, statistics related to type of injury, as well as other contextual factors.

As motion information is evaluated, a determination can be made at 306 to establish if a deviation has occurred. If a deviation has not occurred, the flow returns to 302 where motion data is continually monitored. On the other hand, if a deviation is detected, appropriate feedback can be generated at 308. In other words, if the evaluation at 304 in conjunction with the decision at 306 identifies a deviation from some defined or pre-programmed criteria, feedback can be generated at 308. This feedback can be of most any form including, but not limited to, vibratory sensation, temperature fluctuation sensation, pressure sensation, force, resistance, among others. Accordingly, at 310, the feedback can be rendered via the haptic device.

The following example is provided to add perspective to the features, functions and benefits of the innovation. Accordingly, this example is not intended to limit the scope of the disclosure in any way. Thus, it will be appreciated that other aspects can be contemplated which are to be included within the scope of this disclosure and claims appended hereto.

Continuing with the aforementioned example of rehabilitation of an injured knee, here, a user can apply a haptic device and commence exercise or other motion (e.g., therapeutic routine). In doing so, motion criteria can be captured and evaluated based upon defined criteria or policy information. For instance, a heath-care professional can prescribe a particular exercise routine which specifies range of motion, extension criteria, etc. While exercising, real-time (or near real-time) data can be evaluated against the routine or policy.

If a deviation exists, haptic feedback can be established and exerted as appropriate. For instance, if a user hyper-extends or moves the limb beyond the predetermined range, feedback can be established and applied to the limb to limit damage and promote effective therapy. This feedback can be rendered as vibratory sensations in such a way so as to feel as if a person is actually exerting force upon the limb. In doing so, vibratory motors, solenoids, servo motors, electro-mechanical dampers, etc. can be used to create the virtual effects. More particularly, the motors and/or solenoids can be arranged in such a way that they emulate the sense of touch. A large solenoid can be activated in an expansion and/or contraction method to emulate pressure. Similarly, smaller solenoids can be arranged in an elliptical manner to emulate fingers of a hand.

Figure 4:
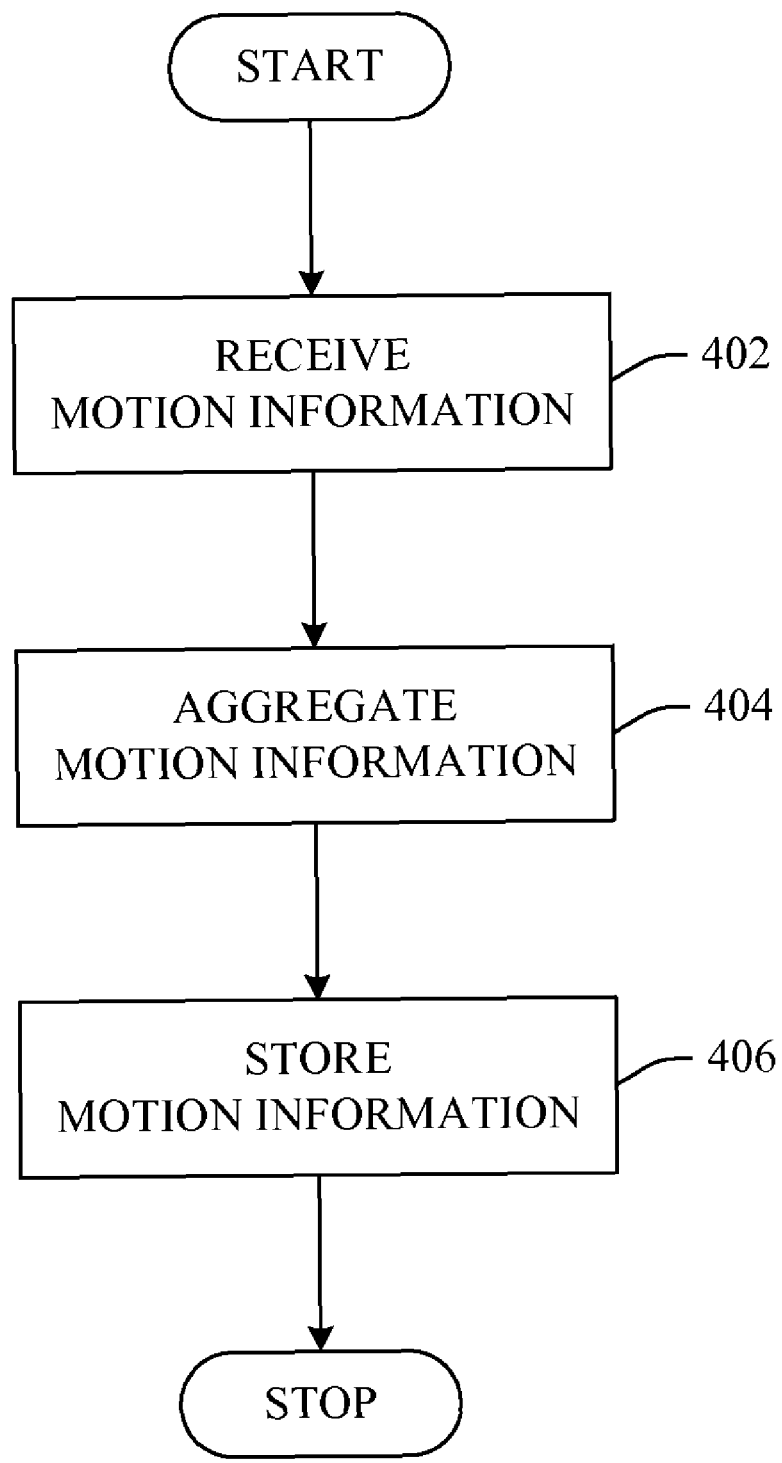
FIG. 4 illustrates an example flow chart of procedures that facilitate passively monitoring motion in accordance with an aspect of the innovation.

FIG. 4 illustrates a methodology of passively monitoring motion in accordance with the innovation. At 402, motion information is received from a haptic device such as a haptic knee brace. As described supra, the information can be actively pushed or pulled from the device in real-time or, alternatively, based upon a defined or inferred schedule. The gathered information can be aggregated at 404 and stored at 406. Alternatively, the motion information can be rendered (e.g., displayed) to a third party such as a health-care specialist.

Figure 5:
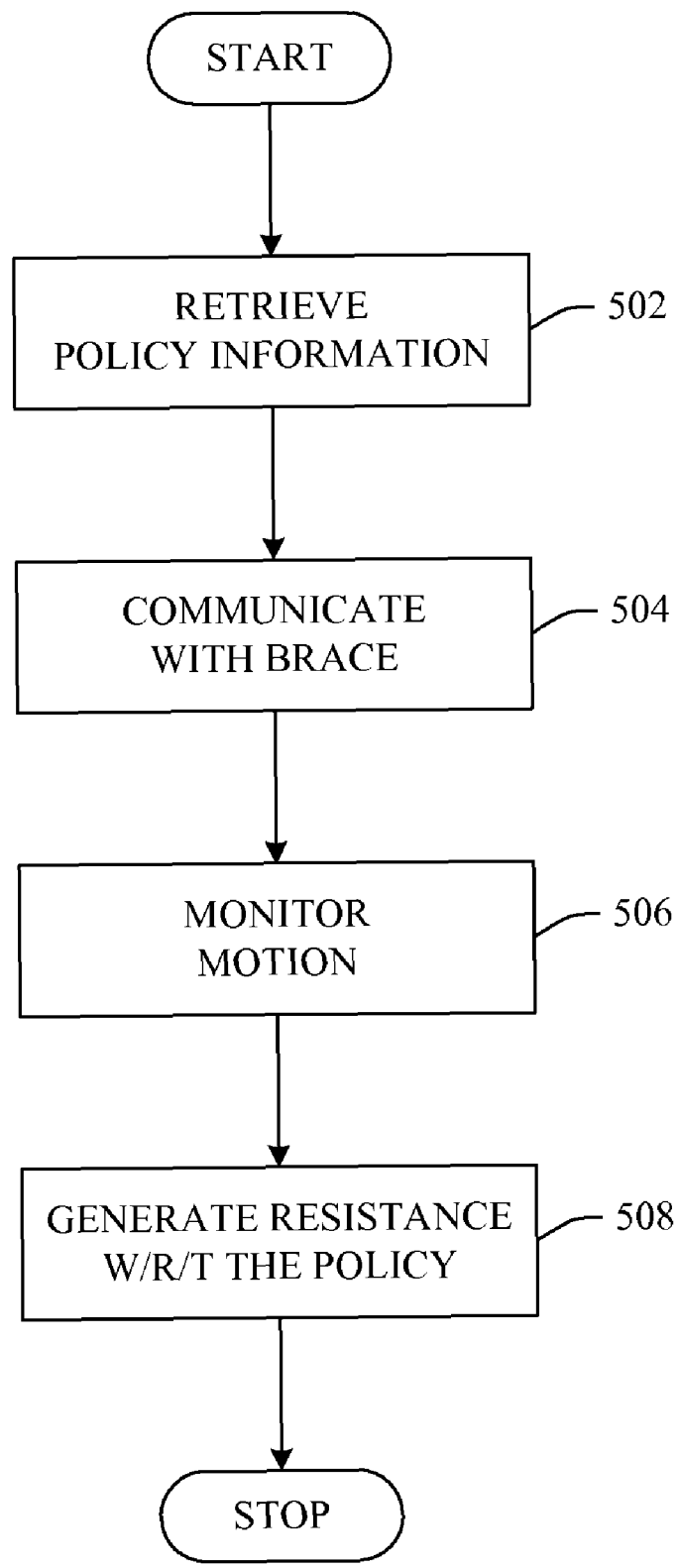
FIG. 5 illustrates an example flow chart of procedures that facilitate generating brace resistance in accordance with an aspect of the innovation.

FIG. 5 illustrates a methodology of establishing resistance force training/exercise in accordance with an aspect of the innovation. At 502, policy information can be retrieved. This policy information can be preprogrammed by a user or third party. As well, the policy information can be established based upon inferences made by an MLR mechanism. In one example, the policy information can be an exercise or therapy routine. This policy information can be communicated to the haptic brace (e.g., knee brace).

At 506, motion can be actively monitored as a user or patient employs the brace. In other words, the device can be equipped with sensory mechanisms that monitor the specific tolerances and ranges of motion by way of the brace. In response, at 508, resistance can be applied in accordance with the policy. For instance, as a user tries to hinge their knee in an upward or outward direction, the brace can automatically apply counter-resistance to promote strength training and/or rehabilitation of ligaments and/or muscles.

Essentially, FIGS. 2, 3, 4 and 5 illustrate methodologies for using haptic devices (e.g., braces) for use in response to illness as well as strength training. More particularly, the figures can be viewed as a progression continuum whereby a patient starts with active drive by the brace (e.g., FIG. 2) and ends with strength training via resistance (e.g., FIG. 5). With regard to illness, in one example, these devices can be applied throughout the course of physical therapy. In doing so, the brace can be prescribed to promote rehabilitation. As such, the brace can be used in a patient's home to essentially act as a virtual physical therapist. As described above, information can be recorded, feedback can be applied to promote compliance, resistance and/or forced feedback can be applied to promote strength training, etc.

With regard to strength training, the feature, functions and benefits of the innovation can be integrated into workout machines. Accordingly, these machines can be instrumented in such a way so as to provide the monitoring, recordation and compliance establishment functionality as described above.

Whether for illness or strength training (or other purpose), the haptic device described herein can also be equipped to wirelessly connect to a home network thereby enabling comprehensive virtual coaching as well as information maintenance and exchange.

In aspects, it is to be understood that feedback (e.g., notice, force, resistance) can vary from patient to patient, injury to injury, injury to recovery time (e.g., rehabilitation progression), etc. In other words, the system can adapt to most any context associated with a procedure or activity. In doing so, the innovation can employ MLR mechanisms to dynamically adapt to a particular context.

In operation, MLR mechanisms can be employed which facilitate automating one or more features in accordance with the subject innovation. The subject innovation (e.g., in connection with establishing appropriate feedback) can employ various MLR-based schemes for carrying out various aspects thereof. For example, a process for determining which type of feedback or when to apply feedback can be facilitated via an automatic classifier system and process.

A classifier is a function that maps an input attribute vector, $x=(x1, x2, x3, x4, xn)$, to a confidence that the input belongs to a class, that is, $f(x)=\text{confidence(class)}$. Such classification can employ a probabilistic and/or statistical-based analysis (e.g., factoring into the analysis utilities and costs) to prognose or infer an action that a user desires to be automatically performed.

A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated from the subject specification, the subject innovation can employ classifiers that are explicitly trained (e.g., via a generic training data) as well as implicitly trained (e.g., via observing user behavior, receiving extrinsic information). For example, SVM's are configured via a learning or training phase within a classifier constructor and feature selection module. Thus, the classifier(s) can be used to automatically learn and perform a number of functions, including but not limited to determining according to a predetermined criteria when to apply feedback based upon a particular context (e.g., time, stage in rehabilitation, age, stamina, amount of sleep obtained, type/amount of food ingested, medications), type/amount of feedback based upon context, when to capture motion data, etc.

Figure 6:
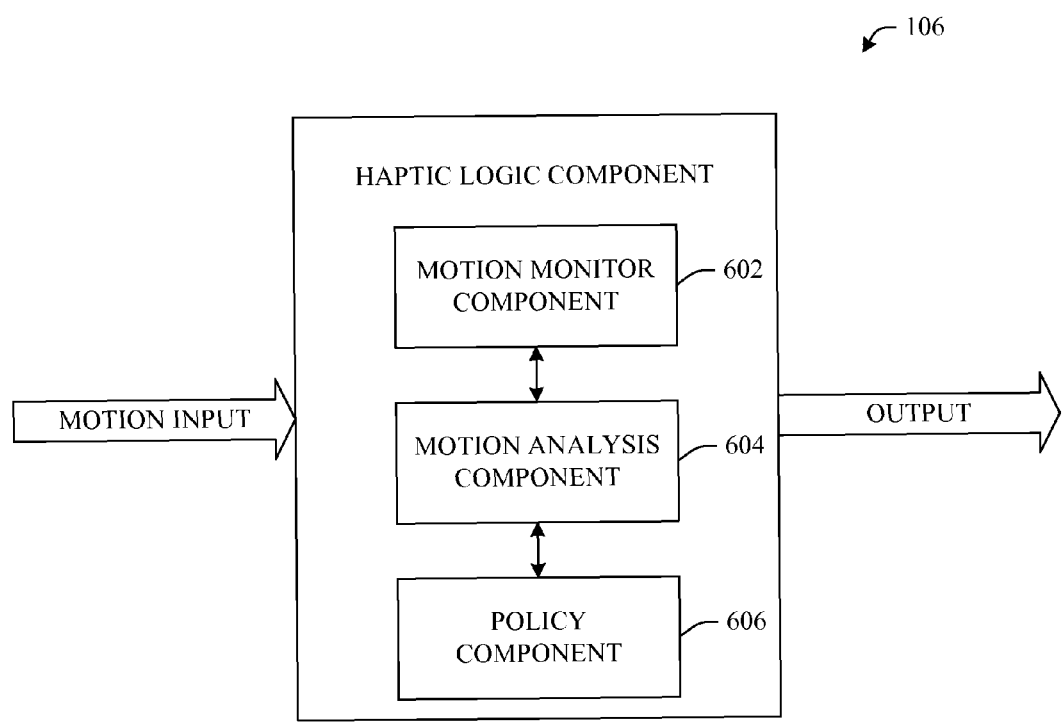
FIG. 6 illustrates an example haptic logic component in accordance with an aspect of the innovation.

With reference now to FIG. 6, an example haptic logic component 106 is shown. Generally, the logic component 106 can include a motion monitor component 602 and a motion analysis component 604. Effectively, the logic component 106, along with the subcomponents (602, 604), establish information by which feedback can be generated as described above. Accordingly, the brace component (104 of FIG. 1) can render the feedback in the course of therapy or training.

The motion monitor component 602 can actively monitor movements by way of the brace component (104 of FIG. 1). In operation, the movements can be monitored in real-time (or near real-time) as desired. The movements (or motion data) can be evaluated by the motion analysis component 604. Here, the analysis component 604 can evaluate the motion data in accordance with a defined or inferred policy or set of criteria (606). Essentially, the analysis component 604 can determine if a deviation occurred or if feedback should be applied based upon a movement pattern and/or context.

Figure 7:
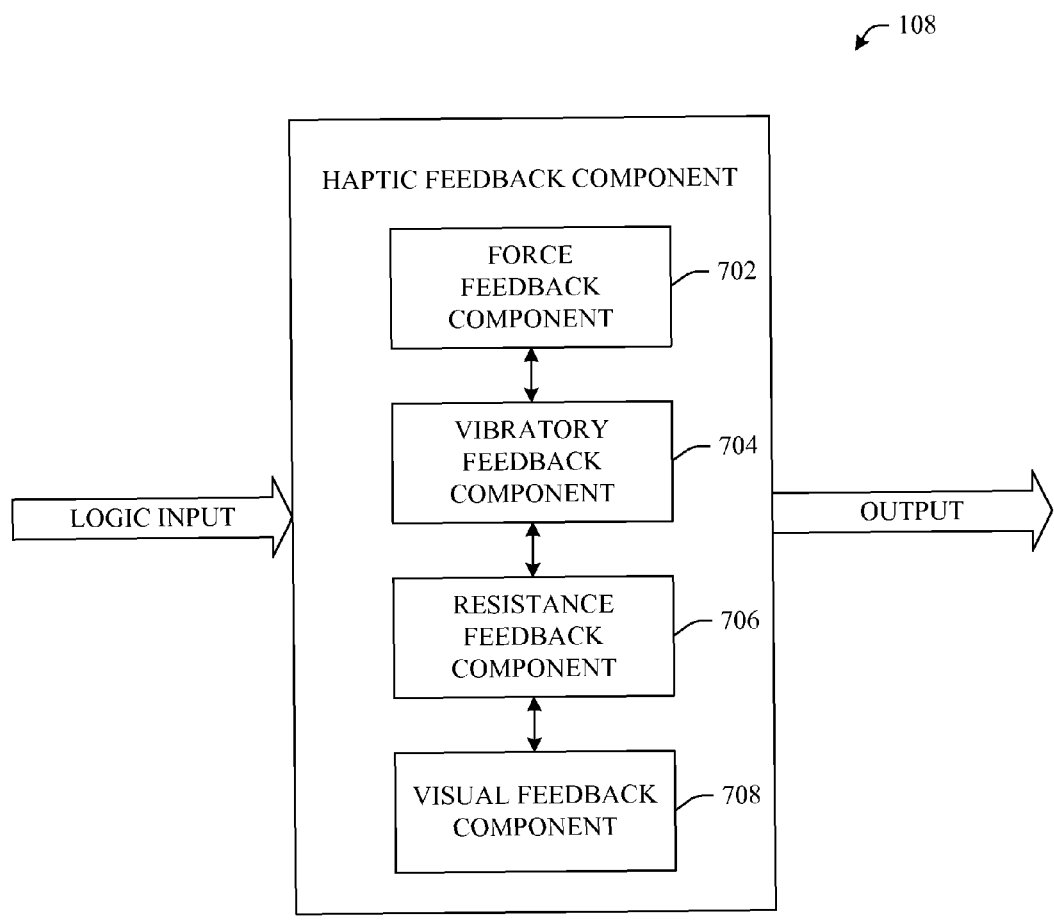
FIG. 7 illustrates an example haptic feedback component in accordance with an aspect of the innovation.

Referring now to FIG. 7, an example block diagram of a haptic feedback component 108 is shown. As illustrated, the haptic feedback component 108 can include a force feedback component 702, a vibratory feedback component 704, a resistance feedback component 706 and a visual feedback component 708 each of which facilitate generation of the appropriate feedback based upon a logic input. In other words, as motion is analyzed, a logic input can be sent to the haptic feedback component 108 which in turn generates appropriate feedback.

In operation, the feedback can be generated and applied to assist in compliance with a predefined policy. For instance, in the example of a haptic knee brace, force feedback can be applied to avoid hyper or overextension of a user's knee joint. Similarly, vibratory feedback can be applied to simulate human touch so as to further promote compliance with are prescribed policy. In other aspects, resistance can be applied to promote strength training and/or rehabilitation.

In addition to haptic feedback, the innovation also provides for other types of feedback such as visual or audible. Visual feedback component 708 can render a graphical display related to performance, compliance, progress, status, etc. For example, while the haptic brace can provide real-time virtual coaching to promote compliance, a visual display or rendering can be provide to further inform a user of performance, compliance, progress, status, etc.

Figure 8:
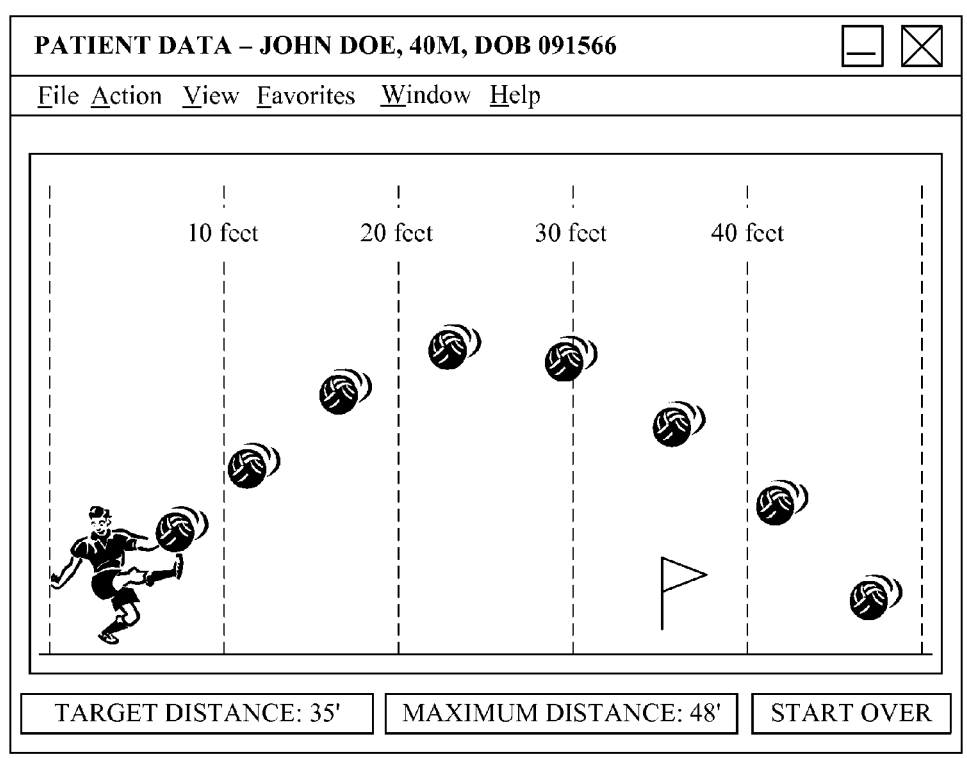
FIG. 8 illustrates an example graphical user interface in accordance with an aspect of the innovation.

Continuing with the example of rehabilitation of an injured knee joint, FIG. 8 illustrates a graphical representation that can translate motion into action. In other words, as force and/or resistance are applied via the brace, the user interface of FIG. 8 can translate the simple action of flexing a knee joint into an act of kicking a ball. As illustrated, a target distance (e.g., 35 feet) can be identified by a flag. While a user hinges their knee joint, the system can translate this action into a graphic of kicking a ball. Here, as the force increases, the ball can be kicked farther. The force and/or resistance can be increased until the target distance is reached. Furthermore, the target distance can represent the minimum performance whereby a maximum distance can be an indicator of performance.

Although the examples described herein are related to a knee joint, it is to be understood that the features, functions and benefits described herein can be applied to most any health-related bracing device including but, not limited to, knee braces, ankle braces, elbow braces, wrist braces, back braces, neck braces or the like. Accordingly, these alternative aspects are to be included within the scope of this disclosure and claims appended hereto.

Figure 9:
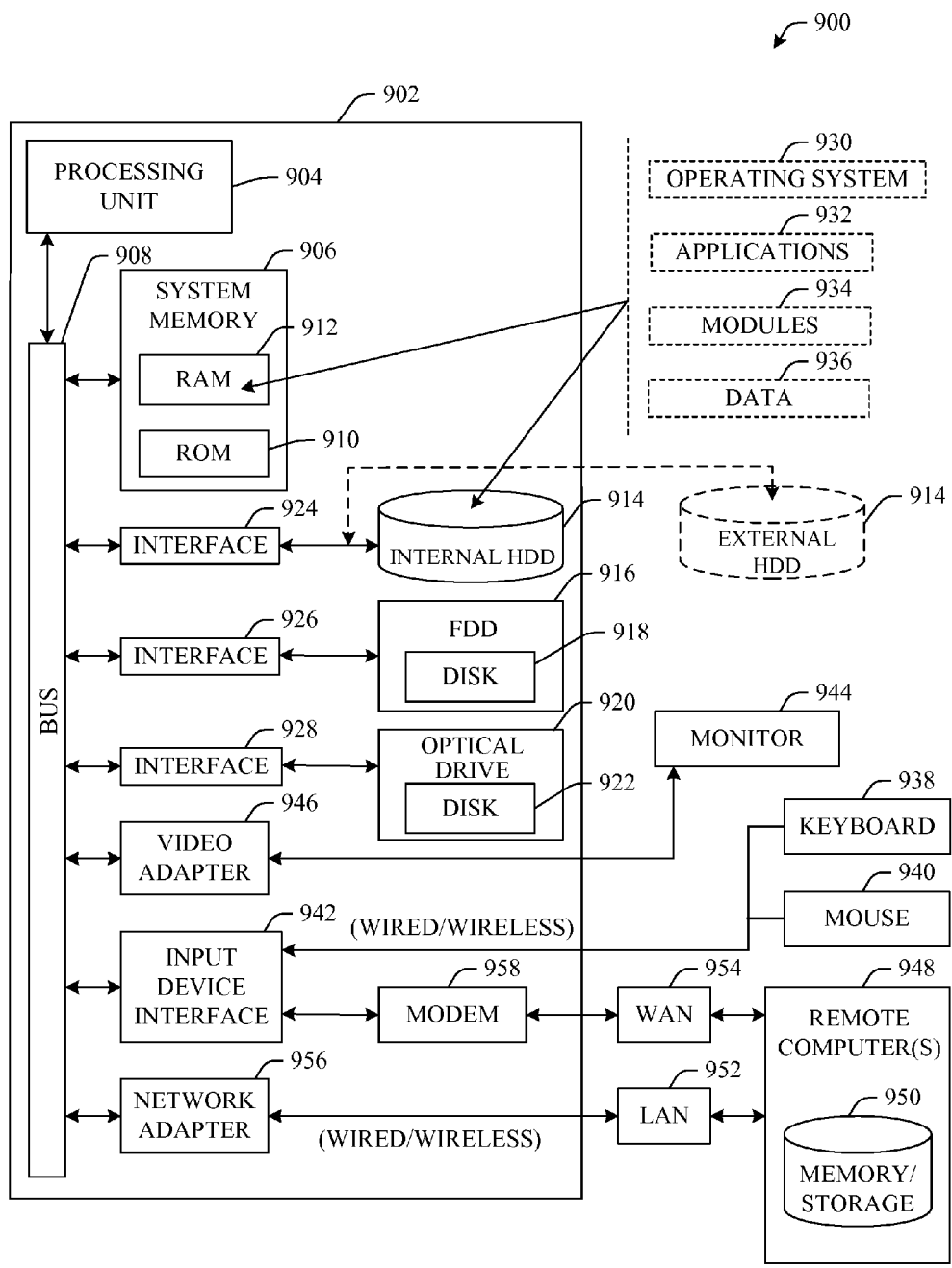
FIG. 9 illustrates a block diagram of a computer operable to execute the disclosed architecture.

Referring now to FIG. 9, there is illustrated a block diagram of a computer operable to execute the disclosed architecture. In order to provide additional context for various aspects of the subject innovation, FIG. 9 and the following discussion are intended to provide a brief, general description of a suitable computing environment 900 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 9, the example environment 900 for implementing various aspects of the innovation includes a computer 902, the computer 902 including a processing unit 904, a system memory 906 and a system bus 908. The system bus 908 couples system components including, but not limited to, the system memory 906 to the processing unit 904. The processing unit 904 can be any of various commercially available processors. Dual microprocessors and other multi-processor architectures may also be employed as the processing unit 904.

The system bus 908 can be any of several types of bus structure that may further interconnect to a memory bus (with or without a memory controller), a peripheral bus, and a local bus using any of a variety of commercially available bus architectures. The system memory 906 includes read-only memory (ROM) 910 and random access memory (RAM) 912. A basic input/output system (BIOS) is stored in a non-volatile memory 910 such as ROM, EPROM, EEPROM, which BIOS contains the basic routines that help to transfer information between elements within the computer 902, such as during start-up. The RAM 912 can also include a high-speed RAM such as static RAM for caching data.

The computer 902 further includes an internal hard disk drive (HDD) 914 (e.g., EIDE, SATA), which internal hard disk drive 914 may also be configured for external use in a suitable chassis (not shown), a magnetic floppy disk drive (FDD) 916, (e.g., to read from or write to a removable diskette 918) and an optical disk drive 920, (e.g., reading a CD-ROM disk 922 or, to read from or write to other high capacity optical media such as the DVD). The hard disk drive 914, magnetic disk drive 916 and optical disk drive 920 can be connected to the system bus 908 by a hard disk drive interface 924, a magnetic disk drive interface 926 and an optical drive interface 928, respectively. The interface 924 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 902, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the example operating environment, and further, that any such media may contain computer-executable instructions for performing the methods of the innovation.

A number of program modules can be stored in the drives and RAM 912, including an operating system 930, one or more application programs 932, other program modules 934 and program data 936. All or portions of the operating system, applications, modules, and/or data can also be cached in the RAM 912. It is appreciated that the innovation can be implemented with various commercially available operating systems or combinations of operating systems.

A user can enter commands and information into the computer 902 through one or more wired/wireless input devices, e.g., a keyboard 938 and a pointing device, such as a mouse 940. Other input devices (not shown) may include a microphone, an IR remote control, a joystick, a game pad, a stylus pen, touch screen, or the like. These and other input devices are often connected to the processing unit 904 through an input device interface 942 that is coupled to the system bus 908, but can be connected by other interfaces, such as a parallel port, an IEEE 1394 serial port, a game port, a USB port, an IR interface, etc.

A monitor 944 or other type of display device is also connected to the system bus 908 via an interface, such as a video adapter 946. In addition to the monitor 944, a computer typically includes other peripheral output devices (not shown), such as speakers, printers, etc.

The computer 902 may operate in a networked environment using logical connections via wired and/or wireless communications to one or more remote computers, such as a remote computer(s) 948. The remote computer(s) 948 can be a workstation, a server computer, a router, a personal computer, portable computer, microprocessor-based entertainment appliance, a peer device or other common network node, and typically includes many or all of the elements described relative to the computer 902, although, for purposes of brevity, only a memory/storage device 950 is illustrated.

The logical connections depicted include wired/wireless connectivity to a local area network (LAN) 952 and/or larger networks, e.g., a wide area network (WAN) 954. Such LAN and WAN networking environments are commonplace in offices and companies, and facilitate enterprise-wide computer networks, such as intranets, all of which may connect to a global communications network, e.g., the Internet.

When used in a LAN networking environment, the computer 902 is connected to the local network 952 through a wired and/or wireless communication network interface or adapter 956. The adapter 956 may facilitate wired or wireless communication to the LAN 952, which may also include a wireless access point disposed thereon for communicating with the wireless adapter 956.

When used in a WAN networking environment, the computer 902 can include a modem 958, or is connected to a communications server on the WAN 954, or has other means for establishing communications over the WAN 954, such as by way of the Internet. The modem 958, which can be internal or external and a wired or wireless device, is connected to the system bus 908 via the serial port interface 942. In a networked environment, program modules depicted relative to the computer 902, or portions thereof, can be stored in the remote memory/storage device 950. It will be appreciated that the network connections shown are example and other means of establishing a communications link between the computers can be used.

The computer 902 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11(a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10 BaseT wired Ethernet networks used in many offices.

Figure 10:
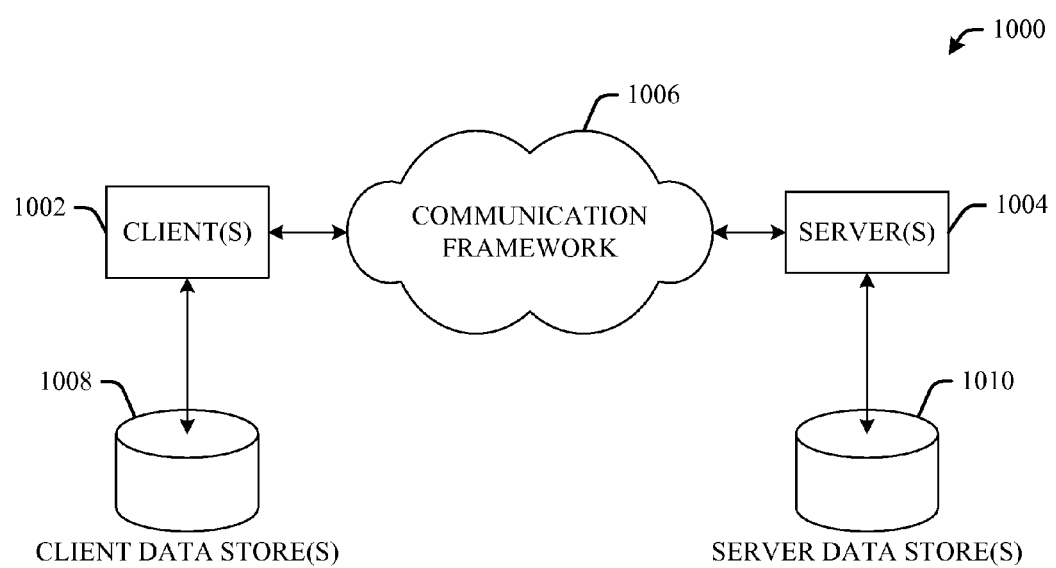
FIG. 10 illustrates a schematic block diagram of an example computing environment in accordance with the subject innovation.

Referring now to FIG. 10, there is illustrated a schematic block diagram of an example computing environment 1000 in accordance with the subject innovation. The system 1000 includes one or more client(s) 1002. The client(s) 1002 can be hardware and/or software (e.g., threads, processes, computing devices). The client(s) 1002 can house cookie(s) and/or associated contextual information by employing the innovation, for example.

The system 1000 also includes one or more server(s) 1004. The server(s) 1004 can also be hardware and/or software (e.g., threads, processes, computing devices). The servers 1004 can house threads to perform transformations by employing the innovation, for example. One possible communication between a client 1002 and a server 1004 can be in the form of a data packet adapted to be transmitted between two or more computer processes. The data packet may include a cookie and/or associated contextual information, for example. The system 1000 includes a communication framework 1006 (e.g., a global communication network such as the Internet) that can be employed to facilitate communications between the client(s) 1002 and the server(s) 1004.

Communications can be facilitated via a wired (including optical fiber) and/or wireless technology. The client(s) 1002 are operatively connected to one or more client data store(s) 1008 that can be employed to store information local to the client(s) 1002 (e.g., cookie(s) and/or associated contextual information). Similarly, the server(s) 1004 are operatively connected to one or more server data store(s) 1010 that can be employed to store information local to the servers 1004.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system configured to facilitate haptic feedback, the system comprising:
   a processor;
   an orthopedic brace component configured to support a joint of a user;
   a haptic logic component configured to sense a characteristic of motion of the joint;
   a haptic feedback component configured to receive an output of a sensed characteristic of the motion of the joint and based, at least, on the output,
   provide haptic feedback via the orthopedic brace component, wherein the haptic feedback is a thermal feedback; and
   a computer-readable storage medium storing instructions that, when executed by the processor, cause the processor to implement at least one of the haptic logic component or the haptic feedback component.

2. The system of claim 1, wherein the joint is at least one of a knee, ankle, elbow, wrist, finger, shoulder, or hip.

3. The system of claim 1, wherein the haptic logic component is further configured to compare the motion of the joint to a policy.

4. The system of claim 3, further comprising a motion monitor component configured to monitor the motion in real-time.

5. The system of claim 4, further comprising a component configured to maintain the policy, wherein the policy is prescribed by a healthcare professional.

6. The system of claim 1, wherein the haptic feedback component is further configured to establish a feedback mechanism based, at least, on motion analysis.

7. The system of claim 6, further comprising a force feedback component configured to generate force via the orthopedic brace component in response to the motion analysis.

8. The system of claim 6, further comprising a vibratory feedback component configured to generate vibratory feedback via the orthopedic brace component based, at least, on the motion analysis, wherein the vibratory feedback is configured to emulate human touch.

9. The system of claim 6, further comprising a resistance feedback component configured to generate resistance via the orthopedic brace component based, at least, on the motion analysis.

10. The system of claim 6, further comprising a visual feedback component configured to display information associated with motion of the orthopedic brace component.

11. The system of claim 1, further comprising a machine learning and reasoning component configured to employ at least one of a probabilistic or a statistical-based analysis to infer an action that the user desires to be automatically performed.

* * * * *